United States Patent [19]

Kasindorf et al.

[11] Patent Number: 5,282,017
[45] Date of Patent: Jan. 25, 1994

[54] REFLECTANCE PROBE

[75] Inventors: Ira Kasindorf, Weston, Conn.; Alexander Stein, Secaucus, N.J.

[73] Assignee: Quantum Logic Corporation, Norwalk, Conn.

[21] Appl. No.: 461,285

[22] Filed: Jan. 5, 1990

[51] Int. Cl.⁵ .............................................. G01N 21/47
[52] U.S. Cl. ...................................... 356/446; 356/43; 356/73.1; 374/126; 250/228
[58] Field of Search ................... 356/43, 44, 48, 73.1, 356/45, 446, 448; 350/551; 374/126; 250/228

[56] References Cited

U.S. PATENT DOCUMENTS

| | | | |
|---|---|---|---|
| 4,225,230 | 9/1980 | Dostoomian et al. | 356/45 |
| 4,313,344 | 2/1982 | Brogardh et al. | 356/44 |
| 4,659,229 | 4/1987 | Hergicz | 356/446 |
| 4,799,787 | 1/1989 | Mason | 356/43 |

*Primary Examiner*—Samuel A. Turner
*Assistant Examiner*—LaCharles P. Keesee

[57] ABSTRACT

Apparatus for measuring the value of the directional spectral hemispherical reflectance of the surface of a target when not engaging but being spaced from the target employs a hollow elongated member having a longitudinal axis and first and second opposite ends. The area of the first end is relatively large relative to that of the second end. The first end is open. The member has an inner chamber extending between the ends and has an inner surface adapted to reflect light falling within a specified wave band. The member when the apparatus is in use is positioned with the first end adjacent but spaced from a selected portion of the surface of the target. The longitudinal axis is oriented essentially normal to a region on the selected surface which would be engaged by a line coincident with the axis and sufficiently extended outwardly from the first end. A beam of light falling within said band is directed within at least a portion of the chamber along the axis and outward through the first end to impinge upon the selected surface portion. A portion of the beam is reflected after said impingement backward through the first end into the chamber. The reflected light which strikes the inner surface of the chamber is directed backwardly within the chamber toward the second end. An electrical signal derived from at least a portion of the backwardly directed light provides a measurement of said reflectance value.

5 Claims, 1 Drawing Sheet

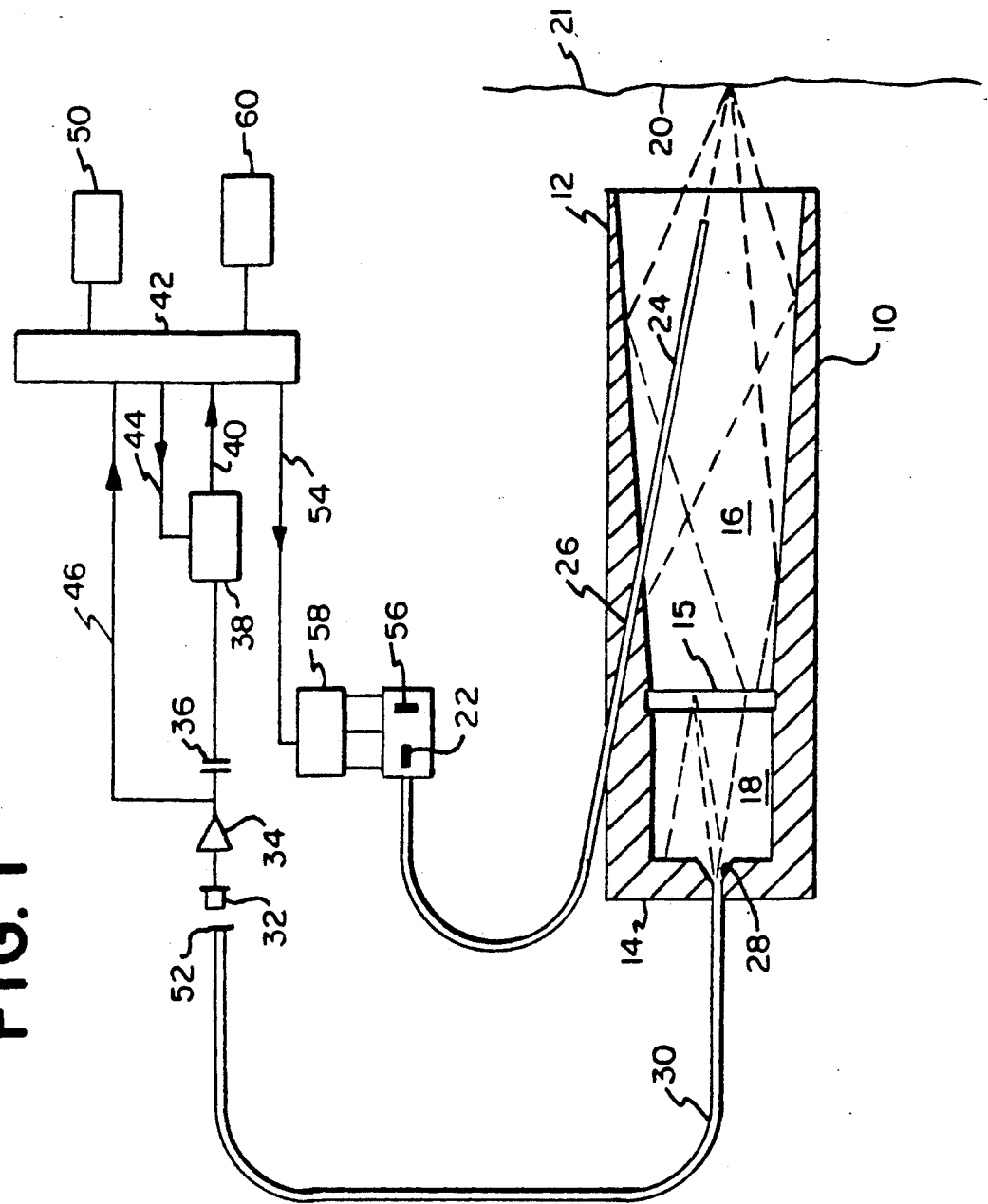

REFLECTANCE PROBE

BACKGROUND OF THE INVENTION

It is known that all physical bodies at temperatures above absolute zero emit electromagnetic radiation whose spectral radiance L at a given wavelength [λ] is described by the Planck formula:

$$L = E2hc^2\lambda^{-5}[\exp\{hc/\lambda kT\} - 1]^{-1}$$

where E is the spectral emittance of the radiating object at this given wavelength; T is the absolute temperature of the object; c is the velocity of light in vacuum; h is the Planck constant; and k is the Boltzmann constant.

It is also known that the spectral emittance E at a given wavelength [λ] of opaque bodies can be determined from a measurement of the directional spectral hemispherical reflectance R at the same given wavelength in accordance with the Kirchhoff principle:

$$E = 1 - R.$$

The directional spectral hemispherical reflectance is defined as the relative radiance power reflected back into hemispherical space when the surface is irradiated by a collimated beam of radiation incident from a particular direction [ɸ,θ], where ɸ is the azimuth and θ is the elevation angle relative to the surface normal. The emittance value E in the Planck formula is that observed in the same direction.

When the values for directional spectral hemispherical reflectance and spectral radiance can be measured directly, the surface temperature of any opaque object can be determined accurately by using the Planck formula and the Kirchhoff principle without touching or interfering in any way with the object of interest. Such measurements have been made by placing a specimen in a specially designed integrating sphere reflectometer and employing laser beam heating and monochromatic irradiation of the specimen with modulated laser light. A detailed description of this procedure is contained in a paper entitled MEASUREMENTS OF SPECTRAL EMISSIVITY OF UO2 ABOVE THE MELTING POINT, by M. Bober and H. U. Karow [Proceedings of the Symposium on Thermophysical Properties, 7th series, U.S. Bureau of Standards; published by Am. Soc. of Mech. Engineers, NYC 1977, pages 344-350].

However, the apparatus described in this paper can only be used with a specimen that can be placed within the integrating sphere. There is a need for an apparatus which can be used to make the same measurements on large objects which cannot be disposed in an integrating sphere.

The present invention is directed toward new portable relatively inexpensive apparatus which can be used not only to obtain a measurement of the directional spectral hemispherical reflectance of an opaque object, but also its temperature, regardless of the surface texture of the object and without contacting or interfering in any way with the object itself.

SUMMARY OF THE INVENTION

In accordance with the principles of the invention, the value of the directional spectral hemispherical reflectance of the surface of a target is measured by portable relatively inexpensive apparatus in such manner that the target is not engaged or interfered with.

To this end, the apparatus employs a hollow elongated member having first and second opposite ends and an interior chamber extending between the ends with the first end open. The inner surface of the chamber is shaped and adapted to receive any light within a specified wave band that is directed into the chamber and also to reflect such light rearward toward the second end.

In use the member is positioned with the first end adjacent but spaced from a selected portion of the surface of the target. The member has a longitudinal axis which is oriented essentially normal to a point on the selected surface which would be engaged by a line coincident with the axis and sufficiently extended outwardly from the first end.

A beam of light falling within said band, such as a laser beam, is directed from a position in the chamber outward through the first end upon said selected surface portion of the target. A portion of the energy of the light beam is reflected after said impingement backwardly through the first end into the chamber. Essentially all of this reflected light energy is directed upon the inner surface of the member and is guided back to the second end.

Means disposed adjacent the second end and responsive to the light guided thereto derives therefrom a first electrical signal which is a measurement of said reflectance value. The spectral emittance can then be calculated from the reflectance value by using the Kirchhoff principle.

When the target is heated to emit spectral radiance at the wavelength band of interest, a portion of this radiance can be directed within the member and guided to the second end. Additional means responsive to the directed and guided radiance can be used to derive therefrom a second signal which is a measurement of the value of the spectral radiance.

After the value of the spectral emittance has been calculated using the Kirchhoff principle and the spectral radiance value has been measured, the absolute temperature of the target can be calculated using the Planck formula, thus obtaining an extremely accurate temperature measurement of the heated target.

BRIEF DESCRIPTION OF THE DRAWING

The accompanying FIGURE illustrates a preferred embodiment of the invention.

DETAILED DESCRIPTION OF PREFERRED EMBODIMENTS

Referring now to the FIGURE, a hollow elongated member 10 has a longitudinal axis and first and second opposite ends 12 and 14. Member 10 can be constructed from steel or other suitable material which is durable in use in a portable instrument. A light diffuser 15 adapted to diffuse light within a specified wave band is positioned in a hollow interior chamber of the member at right angles to the axis and intermediate to the ends. The chamber extends between the first end 12 which is open and the second end 14 which is closed. A portion of the hollow interior chamber in the region 16 between the first end and the diffuser has the shape of a truncated cone, the larger end of the cone being coincident with the first open end. A portion of the hollow interior chamber in the region 18 between the second end and the diffuser has the shape of a circular cylinder, the diameter of the cylinder being essentially the same as the smaller end of the truncated cone.

The inner surface of the hollow member is polished or is otherwise adapted to reflect light falling within the same wave band. In use the member is positioned with the first end adjacent but spaced from a selected portion 20 of the surface of the target 21. The longitudinal axis of the member is oriented essentially normal to a region on the selected surface which would be engaged by a line coincident with the axis and sufficiently extended outwardly from the second end.

A beam of light falling within said band, such as a laser beam, is directed from a laser 22 via a fiber optic cable 24 which extends through a suitable opening 26 in the member located intermediately between the diffuser and the first end and is directed through the first end upon said selected surface portion 20 of the target. A portion of the energy of the light beam is reflected after said impingement and essentially all of the reflected light energy enters through the first end and into the member. The reflected light is directed upon the inner surface of the member and is guided back to the diffuser. The diffuser scatters the light and directs at least a portion of it into a conical opening 28 in the second end. A second fiber optic cable 30 receives the light directed into opening 28 and transmits it to photodetector 32.

The photodetector output is a variable direct current which is supplied to the input of amplifier 34. This amplifier converts the variable direct current into a proportional varible direct voltage. This voltage is supplied through an isolation capacitor 36 to the input of a lock-in amplifier [synchronous detector] 38. The output of amplifier 38 is supplied as an input 40 to microcomputer 42. The output voltage from amplifier 34 is also supplied directly as a second input 46 to microcomputer 42. A timing signal output 44 from the microcomputer is supplied as a control signal to amplifier 38.

The laser beam is modulated by turning the drive current to the laser on and off in periodic fashion. This is accomplished by means of a timing signal 54 supplied to the laser driver 58 from the microcomputer. The timing signal 44, suitably timed by the microcomputer and synchronous to timing signal 54, is used to prevent the amplifier 38 from detecting any signal except that generated by the modulated beam.

When, as in this preferred embodiment, the target is heated and emits spectral radiance at the wavelength band of interest, a portion of this radiance is directed within the member and is guided onto the photodetector in the same manner as the reflected light. This radiance is essentially constant and produces a constant direct current component in the output of the photodetector. The reflected portion of the modulated laser beam produces a variable direct current component in the output of the photodetector. Capacitor 36 blocks the direct current component and passes the variable component so that only the variable component is supplied to amplifier 38. The blocked direct component is supplied directly to the microcomputer via input 46 as direct voltage Vo. To avoid interference from the modulated signal, the laser is turned off when the value of Vo is determined. The output of the microcomputer is supplied to digital display 50.

In order to use this apparatus it must first be calibrated. The apparatus is placed in front of a Bureau of Standards approved reflectance standard such as compressed barium sulfate powder of known hemispherical reflectance value Rc. This known value is manually entered into the microcomputer. The apparatus is then operated and the voltage produced at the output of amplifier 38 is measured as V1 and is also entered into the microcomputer.

The direct voltage Vo produced by amplifier 34 is essentially constant and can be related to the spectral radiation of the target in the specified wave band by a suitable calibration. The radiance measurement used to produce voltage Vo should be made while the laser is shut off to avoid any interference from the modulated signal which could produce inaccuracy in measurement. Function switch 60 can be used to operate the microcomputer 42 for this purpose.

The apparatus is then ready for use with target surface 20. Amplifier 38 then produces an output voltage V2. The spectral emittance of the target at the specified wave band, defined as E, is then computed by the micocomputer in accordance with the formula $E = 1 - [V2/V1]Rc$.

After the value of the spectral emittance has been calculated using the Kirchhoff principle and the spectral radiance value has been measured, the absolute temperature of the target can be calculated by the microcomputer using the Planck formula, thus obtaining an extremely accurate temperature measurement of the heated target. The measurement can be displayed in digital display unit 50 operated by the microcomputer.

A radiance filter 52 can be placed in front of the photodetector to select the appropriate spectral wave band from the intercepted thermal radiation.

In the apparatus thus far described, the laser power level is constant as long as the ambient temperature is constant. When the laser is battery powered, an advantage when the instrument is readily portable, the power level will vary unless otherwise controlled. A suitable control system is shown in the Figure wherein a reference photodetector 56 samples the radiation emitted in backward direction by the laser. Photodetector 56 is built in with the laser into the same sealed package which has three leads. The first lead carries the reference photosignal yielded by the photodetector 56, the second lead carries the laser drive current and the third lead is the common lead. The photosignal is used to regulate the laser drive current via control unit 58 so that the laser power is a constant.

Typical pyrometers operate at wavelengths which range from the visible to the far infrared spectrum. Various light sources [including lasers], radiation filters and detectors are available commercially to cover the practically useful range.

The laser could be positioned in the opening 26 and the corresponding fiber optic cable 24 could be eliminated. It is also possible to position the photodetector in an opening in end 14. Because of the proximity of the hot target 21, it is not always practical to place the laser and the photodetector near the member 10. Fiber optic cable connections to the remotely located laser and photodetector are usually preferred.

The diffuser causes the relatively small portion of the entire amount of reflected light impinging upon opening 28 to be an averaging portion of the entire amount, thus eliminating spurious effects.

What is claimed is:

1. Apparatus for measuring the value of the directional spectral hemispherical reflectance and spectral radiance of the surface of a target when not engaging but being spaced from the target, said target being heated to emit thermal radiation at wavelengths falling within a specified wavelength band, said apparatus comprising:

a hollow elongated member having a longitudinal axis and first and second opposite ends, the area of the first end being relatively large relative to that of the second end, one of said first and second ends being open, the member having an inner chamber extending between the ends and having an inner surface adapted to reflect light falling within said wavelength band, said member when the apparatus is in use being positioned with the open end adjacent but spaced from a selected portion of the surface of the target and the longitudinal axis being oriented essentially normal to a region on the selected surface which would be engaged by a line coincident with the axis and sufficiently extended outwardly from the first end;

first means for directing a beam of light falling within said band within at least a portion of the chamber and outward through the open end to impinge upon said selected surface region, a portion of the beam being reflected after said impingement backward through the open end into the chamber, the reflected light which strikes the inner surface of the chamber being directed backwardly within the chamber, from the open end toward the other end, a portion of the emitted radiation being directed into the chamber and guided to the other end;

second means responsive to at least a portion of the backwardly directed light to derive therefrom a first electrical signal which is a measurement of said reflectance value; and third means responsive to the directed portion of the thermal radiation to derive therefrom a second electrical signal which is a measurement of the value of said thermal radiation.

2. Apparatus as set forth in claim 1 further including a diffuser disposed in the inner chamber intermediate the other end of the member and said directed light beam.

3. Apparatus as set forth in claim 1 wherein the beam is a laser beam.

4. Apparatus of claim 1 further including fourth means responsive to the first and second signals to derive therefrom an output signal which is a calculated value of the temperature of the target.

5. Apparatus of claim 1 wherein the first means also modulates the light beam, the second means responds only to the modulated beam, and the third means is non-responsive to the modulated beam.

* * * * *